(12) United States Patent
Lobo et al.

(10) Patent No.: US 12,137,934 B2
(45) Date of Patent: Nov. 12, 2024

(54) SURGICAL ACCESS DEVICE WITH FIXATION MECHANISM

(71) Applicant: Covidien LP, Mansfield, MA (US)

(72) Inventors: Astley C. Lobo, West Haven, CT (US); Jason Mickus, Avon, CT (US); Kevin M. Desjardin, Prospect, CT (US)

(73) Assignee: Covidien LP, Mansfield, MA (US)

( * ) Notice: Subject to any disclaimer, the term of this patent is extended or adjusted under 35 U.S.C. 154(b) by 1025 days.

(21) Appl. No.: 17/101,135

(22) Filed: Nov. 23, 2020

(65) Prior Publication Data

US 2022/0160393 A1 May 26, 2022

(51) Int. Cl.
*A61B 17/34* (2006.01)
*A61B 17/00* (2006.01)

(52) U.S. Cl.
CPC ...... *A61B 17/3423* (2013.01); *A61B 2017/00876* (2013.01); *A61B 2017/346* (2013.01)

(58) Field of Classification Search
CPC ...... A61B 2017/346; A61B 2017/3464; A61B 2017/3433; A61B 2017/348; A61B 2017/3482; A61B 2017/3484; A61B 2017/3486; A61B 2017/3492; A61B 2017/3441; A61B 2017/00876; A61B 2017/00637; A61B 2017/3419; A61B 2017/3454; A61B 17/3431; A61B 17/3421; A61B 17/3423; A61B 17/3439; A61B 17/3417; A61B 17/34; A61M 39/02; A61M 39/0208; A61M 39/06; A61M 39/0613; A61M 39/0247; A61M 2039/0202;

(Continued)

(56) References Cited

U.S. PATENT DOCUMENTS

| 397,060 A | 1/1889 | Knapp |
| 512,456 A | 1/1894 | Sadikova |

(Continued)

FOREIGN PATENT DOCUMENTS

| EP | 0480653 A1 | 4/1992 |
| EP | 0610099 A2 | 8/1994 |

(Continued)

OTHER PUBLICATIONS

Extended European Search Report dated Mar. 31, 2022 issued in corresponding EP Appln. No. 21209207.6.

*Primary Examiner* — Kevin C Sirmons
*Assistant Examiner* — Alexandra Lalonde
(74) *Attorney, Agent, or Firm* — Draft Masters IP, LLC

(57) ABSTRACT

A surgical access device includes a cannula body, an obturator assembly, and a fixation mechanism. The fixation mechanism includes at least one wing, a first plurality of magnets disposed on an elongated portion of the obturator assembly, and a second plurality of magnets disposed on the at least one wing. The at least one wing is coupled to an elongated portion of the cannula body and is movable between a first position where the at least one wing is parallel to a longitudinal axis, and a second position where the at least one wing is disposed at an angle to the longitudinal axis. A predetermined amount of translation of the elongated portion of the obturator assembly within a channel of the elongated portion of the cannula body causes the at least one wing to move from the first position to the second position.

18 Claims, 15 Drawing Sheets

(58) Field of Classification Search
CPC .. A61M 2039/0205; A61M 2039/0223; A61M 2039/0261; A61M 2039/0267; A61M 2039/0273; A61M 2039/0276; A61M 2039/0297; A61M 2039/062; A61M 2039/0633; A61M 2039/0626; A61M 2039/0686; A61M 2039/0258; A61M 2039/0232; A61M 2039/0279; A61M 2039/0291; A61M 2025/0286; A61M 2025/0293; A61M 2025/0079; A61M 2025/0004; A61M 2025/0175; A61M 2205/0272; A61M 2205/6054; A61M 2205/8287; A61M 25/0067; A61M 25/0074; A61M 25/02; A61M 25/04

See application file for complete search history.

(56) References Cited

U.S. PATENT DOCUMENTS

| | | | |
|---|---|---|---|
| 1,213,005 A | 1/1917 | Pillsbury |
| 2,912,981 A | 11/1959 | Keough |
| 2,936,760 A | 5/1960 | Gains |
| 3,039,468 A | 6/1962 | Price |
| 3,050,066 A | 8/1962 | Koehn |
| 3,253,594 A | 5/1966 | Matthews et al. |
| 3,397,699 A | 8/1968 | Kohl |
| 3,545,443 A | 12/1970 | Ansari et al. |
| 3,713,447 A | 1/1973 | Adair |
| 3,774,596 A | 11/1973 | Cook |
| 3,800,788 A | 4/1974 | White |
| 3,882,852 A | 5/1975 | Sinnreich |
| 3,896,816 A | 7/1975 | Mattler |
| 3,961,632 A | 6/1976 | Moossun |
| RE29,207 E | 5/1977 | Bolduc et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,490,137 A | 12/1984 | Moukheibir |
| 4,496,345 A | 1/1985 | Hasson |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,232,446 A | 8/1993 | Arney |
| 5,232,451 A | 8/1993 | Freitas et al. |
| 5,234,454 A | 8/1993 | Bangs |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,656,013 A | 8/1997 | Yoon |
| 5,667,479 A | 9/1997 | Kieturakis |
| 5,667,520 A | 9/1997 | Bonutti |
| 5,704,372 A | 1/1998 | Moll et al. |
| 5,707,382 A | 1/1998 | Sierocuk et al. |
| 5,713,869 A | 2/1998 | Morejon |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,803,901 A | 9/1998 | Chin et al. |

(56) References Cited

U.S. PATENT DOCUMENTS

| | | | |
|---|---|---|---|
| 5,810,867 | A | 9/1998 | Zarbatany et al. |
| 5,814,060 | A | 9/1998 | Fogarty et al. |
| 5,836,913 | A | 11/1998 | Orth et al. |
| 5,836,961 | A | 11/1998 | Kieturakis et al. |
| 5,865,802 | A | 2/1999 | Yoon et al. |
| 5,893,866 | A | 4/1999 | Hermann et al. |
| 5,925,058 | A | 7/1999 | Smith et al. |
| 6,361,543 | B1 | 3/2002 | Chin et al. |
| 6,368,337 | B1 | 4/2002 | Kieturakis et al. |
| 6,375,665 | B1 | 4/2002 | Nash et al. |
| 6,379,372 | B1 | 4/2002 | Dehdashtian et al. |
| 6,432,121 | B1 | 8/2002 | Jervis |
| 6,447,529 | B2 | 9/2002 | Fogarty et al. |
| 6,468,205 | B1 | 10/2002 | Mollenauer et al. |
| 6,506,200 | B1 | 1/2003 | Chin |
| 6,514,272 | B1 | 2/2003 | Kieturakis et al. |
| 6,517,514 | B1 | 2/2003 | Campbell |
| 6,527,787 | B1 | 3/2003 | Fogarty et al. |
| 6,540,764 | B1 | 4/2003 | Kieturakis et al. |
| 6,796,960 | B2 | 9/2004 | Cioanta et al. |
| 7,300,448 | B2 | 11/2007 | Criscuolo et al. |
| 7,691,089 | B2 | 4/2010 | Gresham |
| 8,454,645 | B2 | 6/2013 | Criscuolo et al. |
| 8,926,508 | B2 | 1/2015 | Hotter |
| 10,022,149 | B2 | 7/2018 | Holsten et al. |
| 10,751,086 | B2 | 8/2020 | Shipp et al. |
| 2006/0079925 | A1 | 4/2006 | Kerr |
| 2008/0287740 | A1 | 11/2008 | Weitzner et al. |
| 2010/0081875 | A1* | 4/2010 | Fowler ............... A61B 1/041 600/114 |
| 2010/0261970 | A1* | 10/2010 | Shelton, IV ....... A61B 17/3423 600/203 |
| 2011/0144447 | A1 | 6/2011 | Schleitweiler et al. |
| 2012/0241188 | A1* | 9/2012 | Power ............... A61B 1/00096 242/615.3 |
| 2013/0053782 | A1* | 2/2013 | Shelton, IV ....... A61B 17/3496 604/167.03 |
| 2015/0297260 | A1 | 10/2015 | Kreuz et al. |
| 2016/0038018 | A1 | 2/2016 | Wilson et al. |
| 2019/0059870 | A1* | 2/2019 | Jayne ............... A61B 17/0218 |

FOREIGN PATENT DOCUMENTS

| | | |
|---|---|---|
| EP | 0880939 A1 | 12/1998 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |
| WO | 2016186905 A1 | 11/2016 |

* cited by examiner

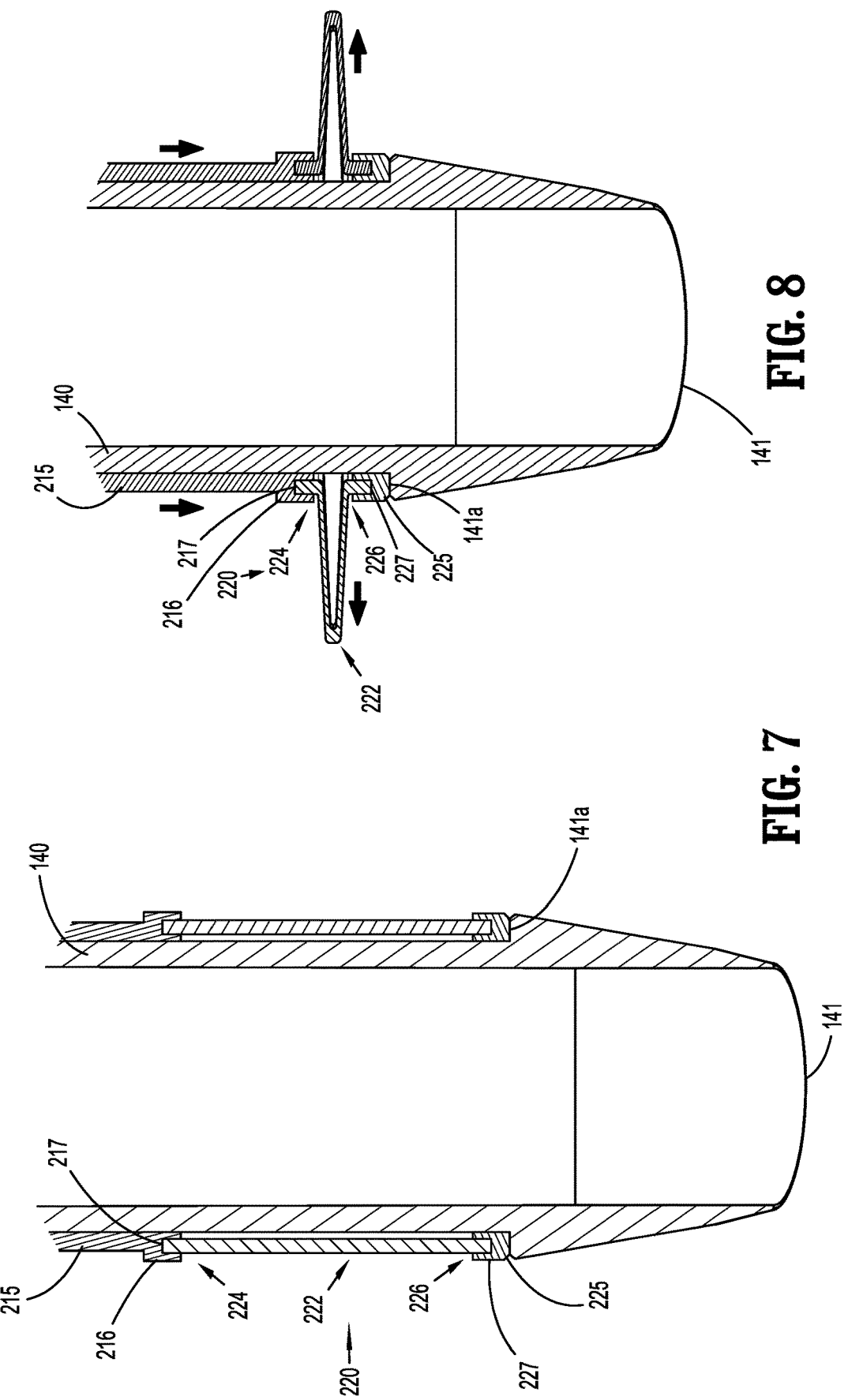

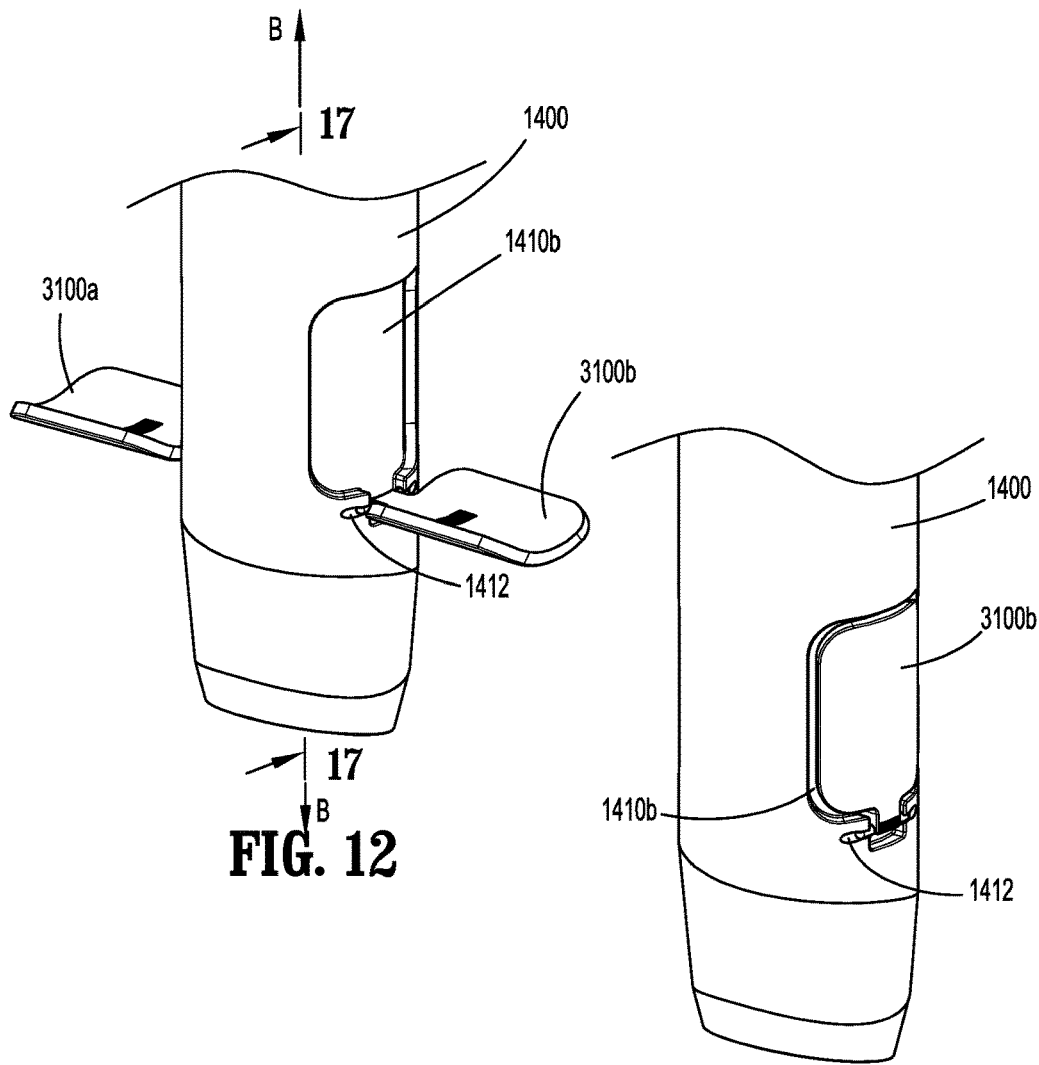
FIG. 12
FIG. 13
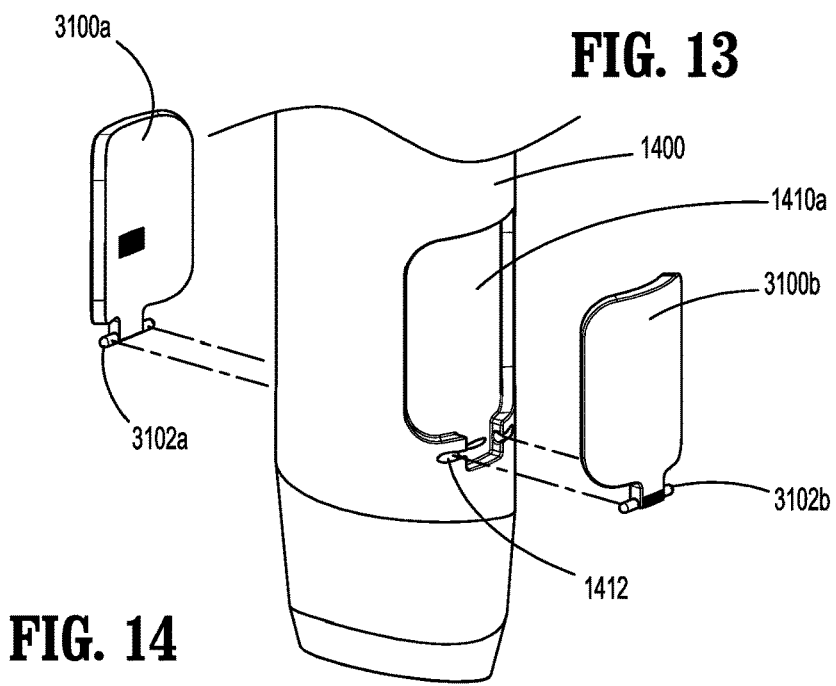
FIG. 14

SURGICAL ACCESS DEVICE WITH FIXATION MECHANISM

BACKGROUND

Technical Field

The present disclosure relates to a surgical access device. More particularly, the present disclosure relates to a surgical access device having a fixation mechanism to help maintain its position relative to a patient during a surgical procedure.

Background of Related Art

In minimally invasive surgical procedures, including endoscopic and laparoscopic surgeries, a surgical access device permits the introduction of a variety of surgical instruments into a body cavity or opening. A surgical access device (e.g., a cannula) is introduced through an opening in tissue (i.e., a naturally occurring orifice or an incision) to provide access to an underlying surgical site in the body. The incision is typically made using an obturator having a blunt or sharp tip that has been inserted within the passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall and is then removed to permit introduction of surgical instrumentation through the surgical access device to perform the surgical procedure.

During these procedures, it may be challenging to maintain the position of the surgical access device with respect to the body wall, particularly when exposed to a pressurized environment. To help maintain the position of the surgical access device with respect to the body wall, an expandable anchor or fixation mechanism disposed near a distal end of the surgical access device is occasionally used. Expanding such an anchor while the surgical access device is within the body helps prevent the surgical access device from undesired movement with respect to the body.

SUMMARY

The present disclosure relates to a surgical access device including a cannula body, an obturator, and a fixation mechanism. The cannula body includes a housing and an elongated portion extending distally from the housing. The elongated portion defines a longitudinal axis, and defines a channel extending therethrough. The obturator assembly includes a housing and an elongated portion extending distally from the housing. At least part of the elongated portion is configured to be inserted through the channel of the elongated portion of the cannula body. The fixation mechanism includes at least one wing, a first plurality of magnets, and a second plurality of magnets. The at least one wing is coupled to the elongated portion of the cannula body, and is movable relative to the elongated portion of the cannula between a first position where the at least one wing is parallel to the longitudinal axis, and a second position where the at least one wing is disposed at an angle to the longitudinal axis. The first plurality of magnets is disposed on the elongated portion of the obturator assembly. The second plurality of magnets is disposed on the at least one wing. A predetermined amount of translation of the elongated portion of the obturator assembly within the channel of the elongated portion of the cannula body causes the at least one wing to move from the first position to the second position.

In disclosed aspects, a predetermined amount of proximal translation of the obturator assembly relative to the cannula body may cause the at least one wing to move from the first position to the second position. In aspects, a predetermined amount of distal translation of the obturator assembly relative to the cannula body may cause the at least one wing to move from the second position to the first position.

In other aspects, the first plurality of magnets may include a first magnet and a second magnet. In aspects, the first magnet of the first plurality of magnets may have a first polarity, and the second magnet of the first plurality of magnets may have a second polarity. The first polarity may be opposite from the second polarity.

In disclosed aspects, the at least one wing may include a wing and a second wing.

In aspects, a first magnet of the first plurality of magnets and a second magnet of the first plurality of magnets may define an annular ring.

In additional aspects, the second plurality of magnets may include a first magnet and a second magnet. In aspects, the first magnet and the second magnet of the second plurality of magnets may have the same polarity as each other. Further, in aspects, the first magnet of the second plurality of magnets may be on an inner surface of the at least one wing, and the second magnet of the second plurality of magnets may be on an outer surface of the at least one wing.

In yet other aspects, the at least one wing may be biased towards the second position.

In aspects, a first magnet and a second magnet of the second plurality of magnets may have the same polarity as each other and as the second magnet of the first plurality of magnets, and the second magnet of the first plurality of magnets may be disposed distally of the second magnet of the first plurality of magnets.

The present disclosure also relates to a surgical access device including a cannula body and a fixation mechanism. The cannula body includes a housing and an elongated portion extending distally from the housing. The elongated portion defines a longitudinal axis, and defines a channel extending therethrough. The fixation mechanism includes a wing and a first magnet. The wing is pivotably engaged with the elongated portion of the cannula body and is movable between a first position where the wing is parallel to the longitudinal axis, and a second position where the wing is disposed at an angle to the longitudinal axis. The first magnet is disposed on the wing. A predetermined amount of translation of an obturator assembly within the channel of the elongated portion of the cannula body causes the wing to move from the first position to the second position.

In disclosed aspects, the surgical access device includes a second magnet disposed on the wing. In aspects, the first magnet is disposed proximally of the second magnet when the wing is in the first position.

In other aspects, when the wing is in the second position, the wing is perpendicular to the longitudinal axis. In aspects, the wing is biased towards the second position.

The present disclosure also relates to a method of deploying a fixation mechanism of a surgical access device. The method includes inserting an elongated portion of an obturator assembly at least partially through a channel of a cannula body, and advancing the obturator assembly distally relative to the cannula body such that a first magnet on the elongated portion of the obturator assembly attracts a first magnet of a wing of the cannula body, causing the wing to pivot relative to the cannula body such that the wing is parallel to a longitudinal axis defined by the channel.

In disclosed aspects, the method may include retracting the obturator assembly proximally relative to the cannula body such that a second magnet on the elongated portion of the obturator assembly repels the first magnet of the wing of the cannula body, causing the wing to pivot relative to the cannula body such that the wing is disposed at an angle to a longitudinal axis. In aspects, advancing the obturator assembly distally relative to the cannula body may cause a second magnet on the elongated portion of the obturator assembly to repel a second magnet of the wing of the cannula body.

DESCRIPTION OF THE DRAWINGS

Various aspects of the present disclosure are illustrated herein with reference to the accompanying drawings, wherein:

FIG. 7 is a longitudinal cross-sectional view of the area of detail indicated in FIG. 6;

FIG. 8 is a longitudinal cross-sectional view of the area of detail indicated in FIG. 9;

FIG. 12 is a perspective view of a distal portion of the surgical access device of FIG. 10 illustrating a portion of the fixation mechanism in a deployed configuration;

FIG. 13 is a perspective view of a distal portion of the surgical access device of FIG. 10 illustrating a portion of the fixation mechanism in an undeployed configuration;

FIG. 14 is an assembly view of a portion of the fixation mechanism of the surgical access device of FIG. 10;

DETAILED DESCRIPTION

Figure 1:
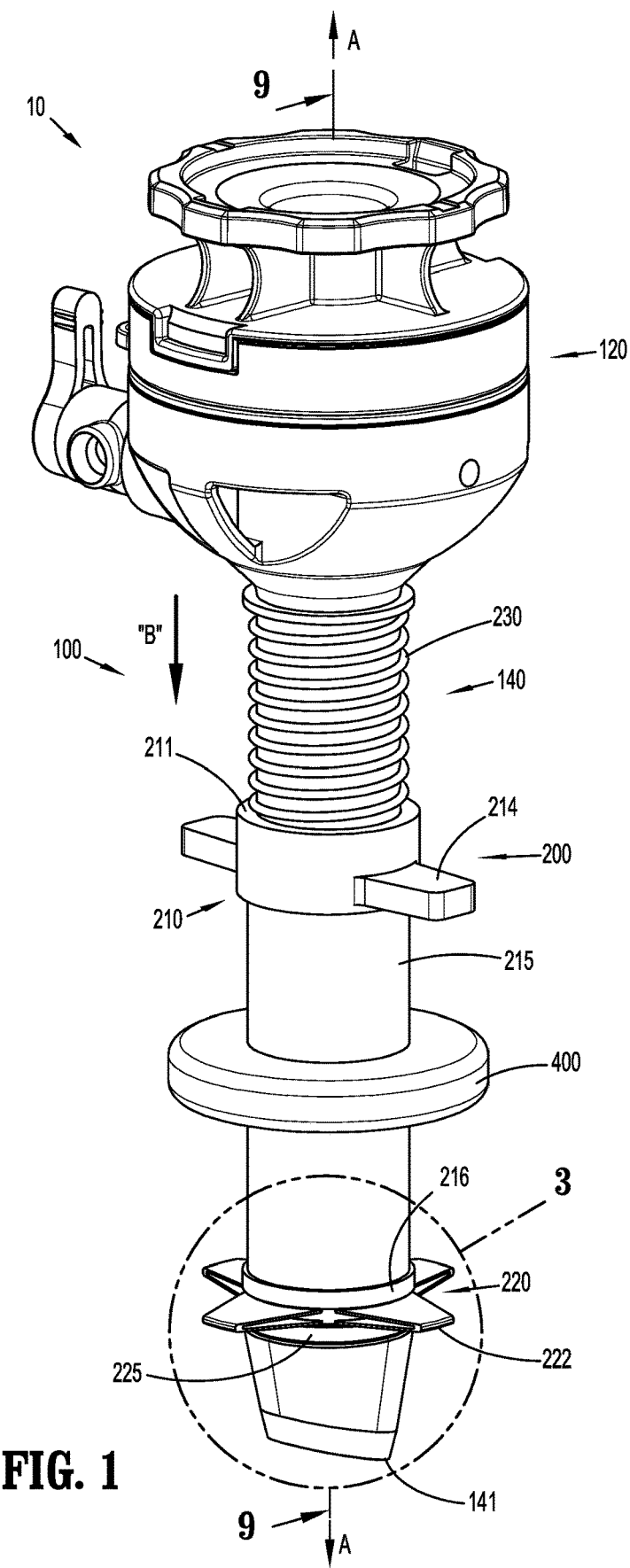
FIG. 1 is a perspective view of a surgical access device illustrating a fixation mechanism in a deployed configuration in accordance with a first aspect of the present disclosure.

Aspects of the presently disclosed surgical access device will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user. As used herein, the terms "parallel" and "perpendicular" are understood to include relative configurations that are substantially parallel and substantially perpendicular up to about +or −10 degrees from true parallel and true perpendicular, respectively, for example.

Generally, the surgical access device or cannula, often part of a trocar assembly, may be employed during surgery (e.g., laparoscopic surgery) and may, in various aspects, provide for the sealed access of laparoscopic surgical instruments into an insufflated body cavity, such as the abdominal cavity. The cannula is usable with an obturator insertable therethrough. The cannula and obturator are separate components but are capable of being selectively connected together. For example, the obturator may be inserted into and through the cannula until the handle of the obturator engages, e.g., selectively locks into, a proximal housing of the cannula. In this initial configuration, the trocar assembly is employed to tunnel through an anatomical structure, e.g., the abdominal wall, either by making a new passage through the structure or by passing through an existing opening through the structure. Once the trocar assembly has tunneled through the anatomical structure, the obturator is removed, leaving the cannula in place in the structure, e.g., in the incision created by the trocar assembly. The proximal housing of the cannula may include seals or valves that prevent the escape of insufflation gases from the body cavity, while also allowing surgical instruments to be inserted into the body cavity.

FIGS. 1-7 illustrate a surgical access device according to a first aspect of the present disclosure. With initial reference to FIGS. 1 and 2, the surgical access device 10 includes a cannula body 100, and a fixation mechanism 200. The cannula body 100 includes a proximal housing 120 at its proximal end and includes an elongated portion 140 extending distally from the proximal housing 120. The elongated portion 140 defines a channel 150 (FIG. 2) extending therethrough, and defines a longitudinal axis "A-A." An obturator (not shown) is insertable through the channel 150 and is engageable with the proximal housing 120, for instance.

For a detailed description of the structure and function of an exemplary surgical access device including a fixation mechanism having a biasing element, please refer to commonly owned U.S. patent application Ser. No. 17/083,916, now U.S. Pat. No. 11,471,189, the content of which is incorporated by reference herein in its entirety.

Figure 9:
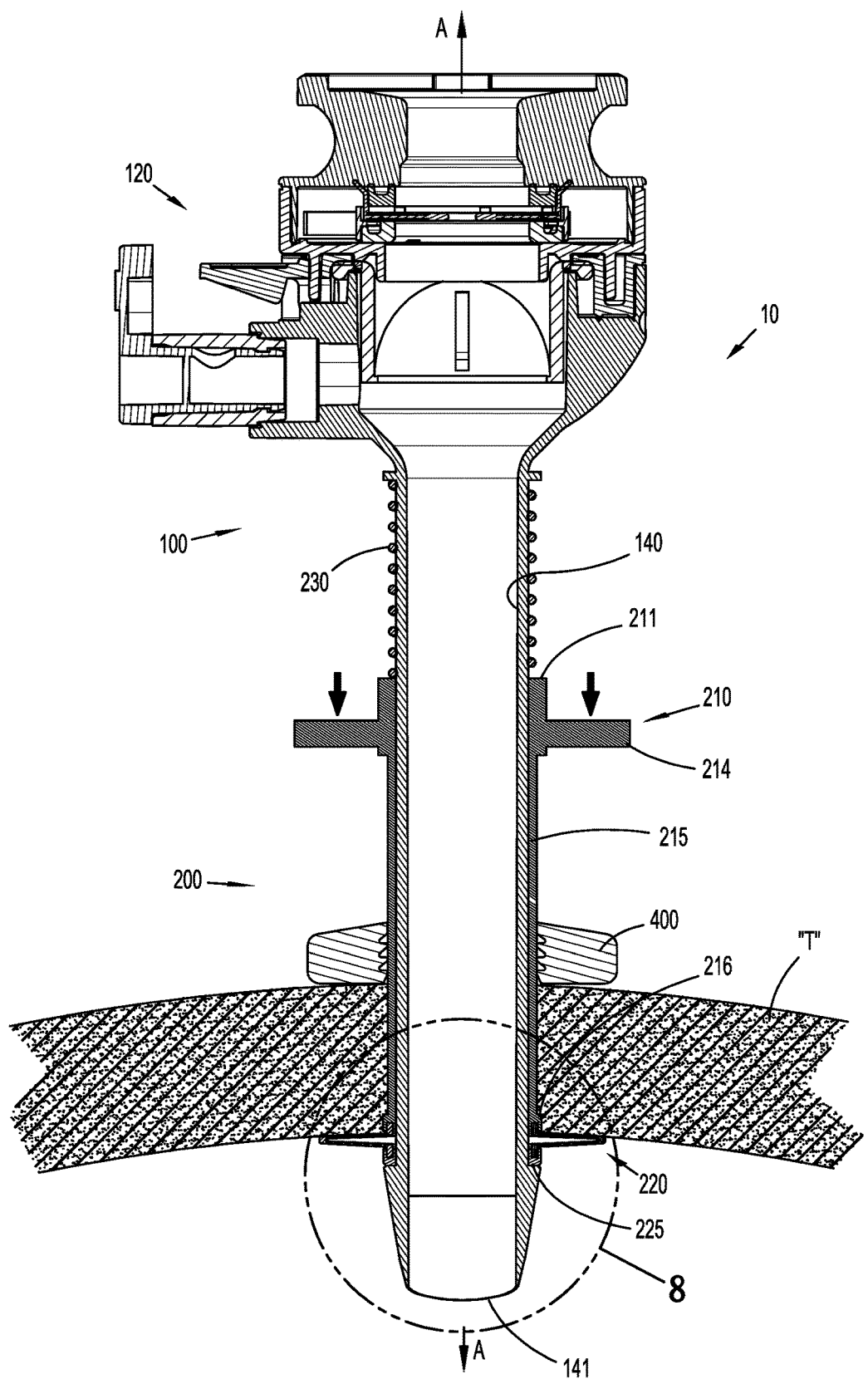
FIG. 9 is a longitudinal cross-sectional view of the surgical access device taken along section line 9-9 in FIG. 1 illustrating a portion of the fixation mechanism within tissue in a deployed configuration.

The fixation mechanism 200 is positionable around the elongated portion 140 of the cannula body 100 such that such that the fixation mechanism 200 radially surrounds a portion of the elongated portion 140. More particularly, portions of the fixation mechanism 200 are longitudinally translatable along the elongated portion 140 between a first position where a proximal part 211 of a collar 210 of the fixation mechanism 200 is farther away from a distal tip 141 of the elongated portion 140 and where a mid-portion 222 of an expandable member 220 of the fixation mechanism 200 is closer to the longitudinal axis "A-A" (FIGS. 5-7), and a second position, where the proximal part 211 of the collar 210 is closer to the distal tip 141 of the elongated portion 140 and where the mid-portion 222 of the expandable member 220 is farther away from the longitudinal axis "A-A" (FIGS. 8 and 9).

Figure 2:
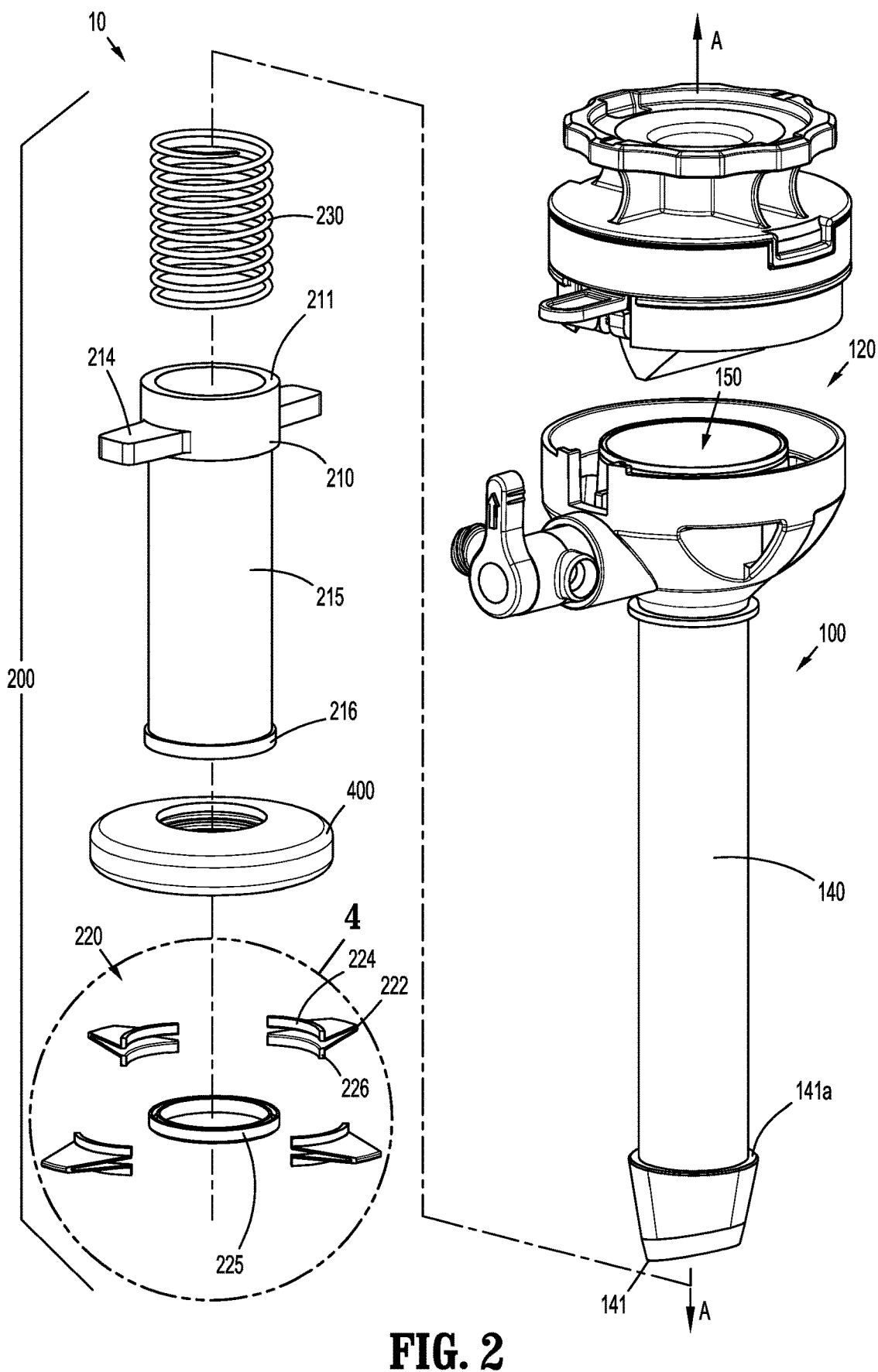
FIG. 2 is an assembly view of the surgical access device of FIG. 1.

Referring to FIGS. 1 and 2, the engagement between the fixation mechanism 200 and the cannula body 100 is shown. The fixation mechanism 200 includes the collar 210, a sleeve 215 extending distally from the collar 210, a proximal ring 216 disposed at a distal end of the sleeve 215, the expandable member 220, a distal ring 225, and a biasing element 230. A proximal end 224 of the expandable member 220 includes a lip that is engaged with (e.g., positioned within a channel of) the proximal ring 216, and a distal end 226 of the expandable member 220 includes a lip that is engaged with (e.g., positioned within a channel 227 of) the distal ring 225 (see FIG. 4).

The collar 210, the sleeve 215, and the proximal ring 216 are longitudinally translatable relative to the elongated portion 140 of the cannula body 100. A lip 141a (FIG. 2) of the distal tip 141 of the elongated portion 140 restricts distal movement of the distal ring 225 relative to the elongated portion 140. Distal movement of the proximal end 224 of the expandable member 220 relative to the elongated portion 140 causes the mid-portion 222 of the expandable member 220 to move away from the longitudinal axis "A-A."

The biasing element 230 (e.g., a compression spring) radially surrounds the elongated portion 140 of the cannula body 100, and is positioned between a distal portion of the proximal housing 120 of the cannula body 100 and a proximal portion of the collar 210 of the fixation mechanism 200. The biasing element 230 biases the collar 210 distally relative to the elongated portion 140, in the general direction of arrow "B" in FIG. 1, such that the expandable member 220 is biased towards its second position (FIGS. 1, 3, 8, and 9). To overcome the bias of the biasing element 230, a user pulls arms 214 of the collar 210 proximally relative to the elongated portion 140, in the general direction of arrow "C" in FIG. 5, such that the expandable member 220 moves towards its first position (FIGS. 5-7).

Figure 3:
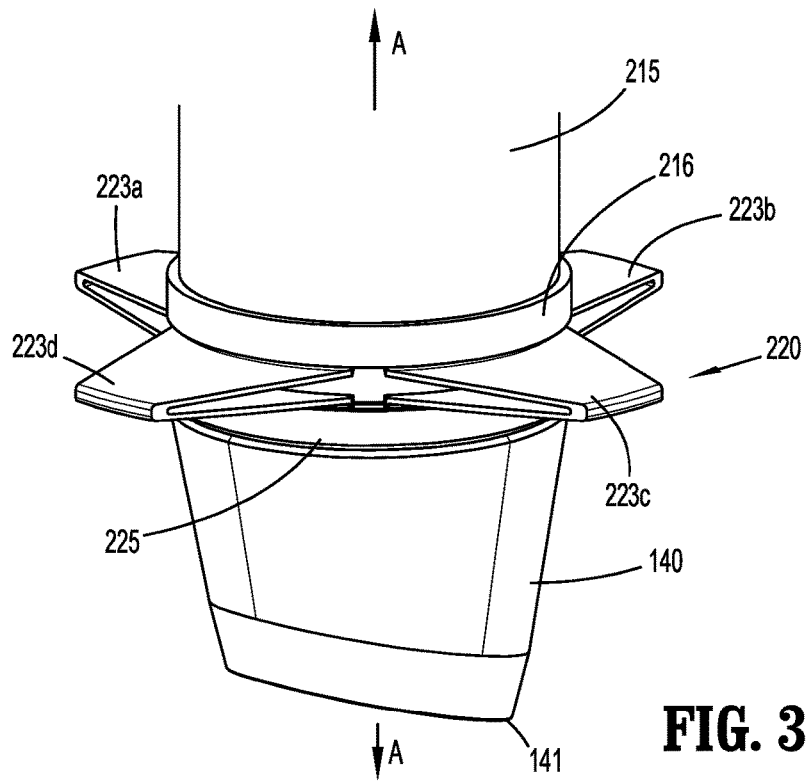
FIG. 3 is a perspective view of the area of detail indicated in FIG. 1.
Figure 4:
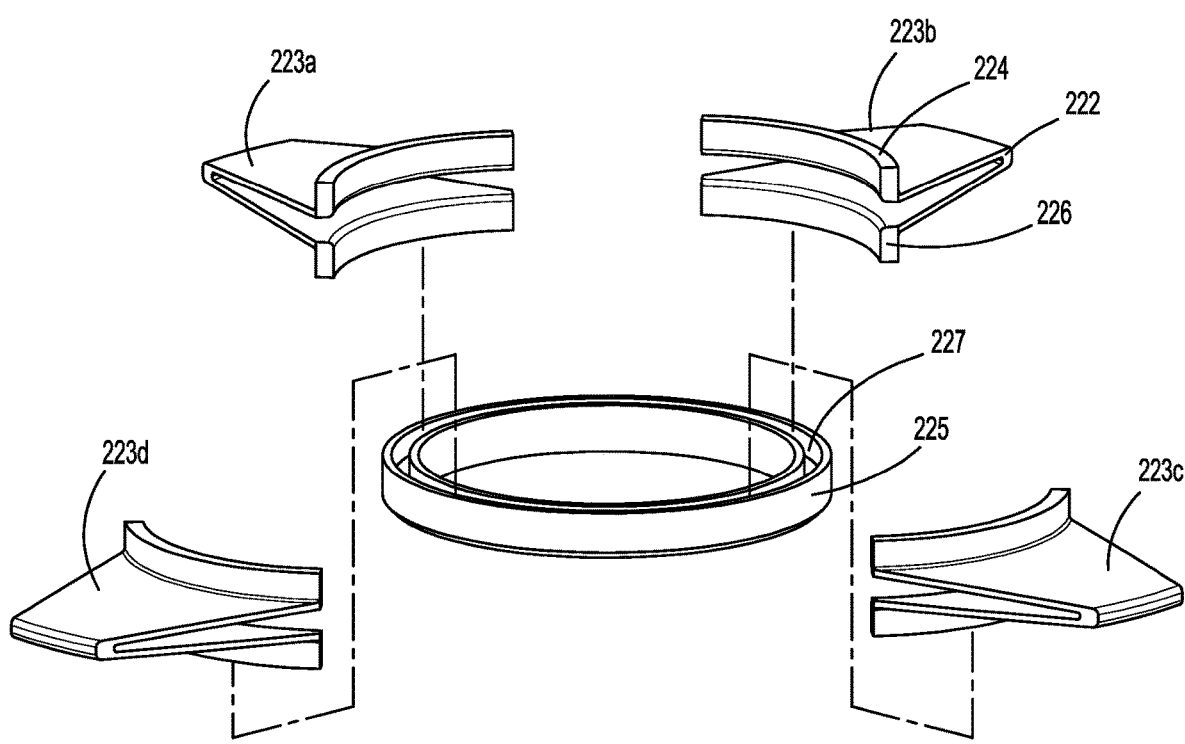
FIG. 4 is a perspective view of the area of detail indicated in FIG. 2.

Referring now to FIGS. 3 and 4, detailed views of the expandable member 220 and the distal ring 225 are shown. In the illustrated aspect, the expandable member 220 includes four sections 223a, 223b, 223c, 223d, which are collectively referred to as section(s) 223. Each section 223 includes the proximal end 224, the mid-portion 222, and the distal end 226. A lip of the proximal end 224 fits at least partially within a channel 217 (FIGS. 7 and 8) of the proximal ring 216, and a lip of the distal end 226 fits at least partially within the channel 227 of the distal ring 225. That is, each section 223 of the expandable member 220 is longitudinally bound between the proximal ring 216 and the distal ring 225. Additionally, each section 223 of the expandable member 220 rotatably engages the proximal ring 216 and the distal ring 225.

Figure 5:
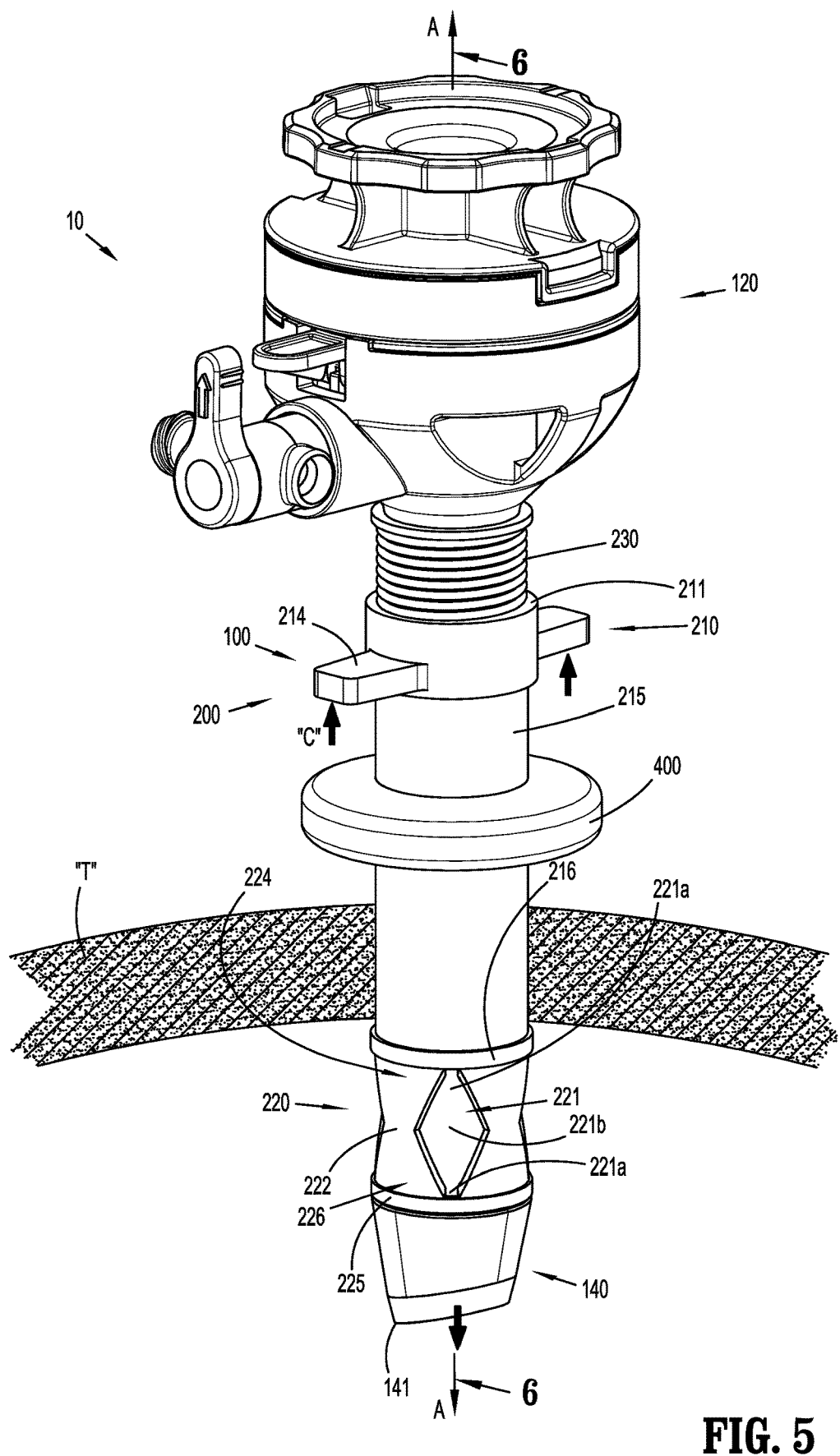
FIG. 5 is a perspective view of the surgical access device of FIG. 1 illustrating a portion of the fixation mechanism within tissue in an undeployed configuration.
Figure 6:
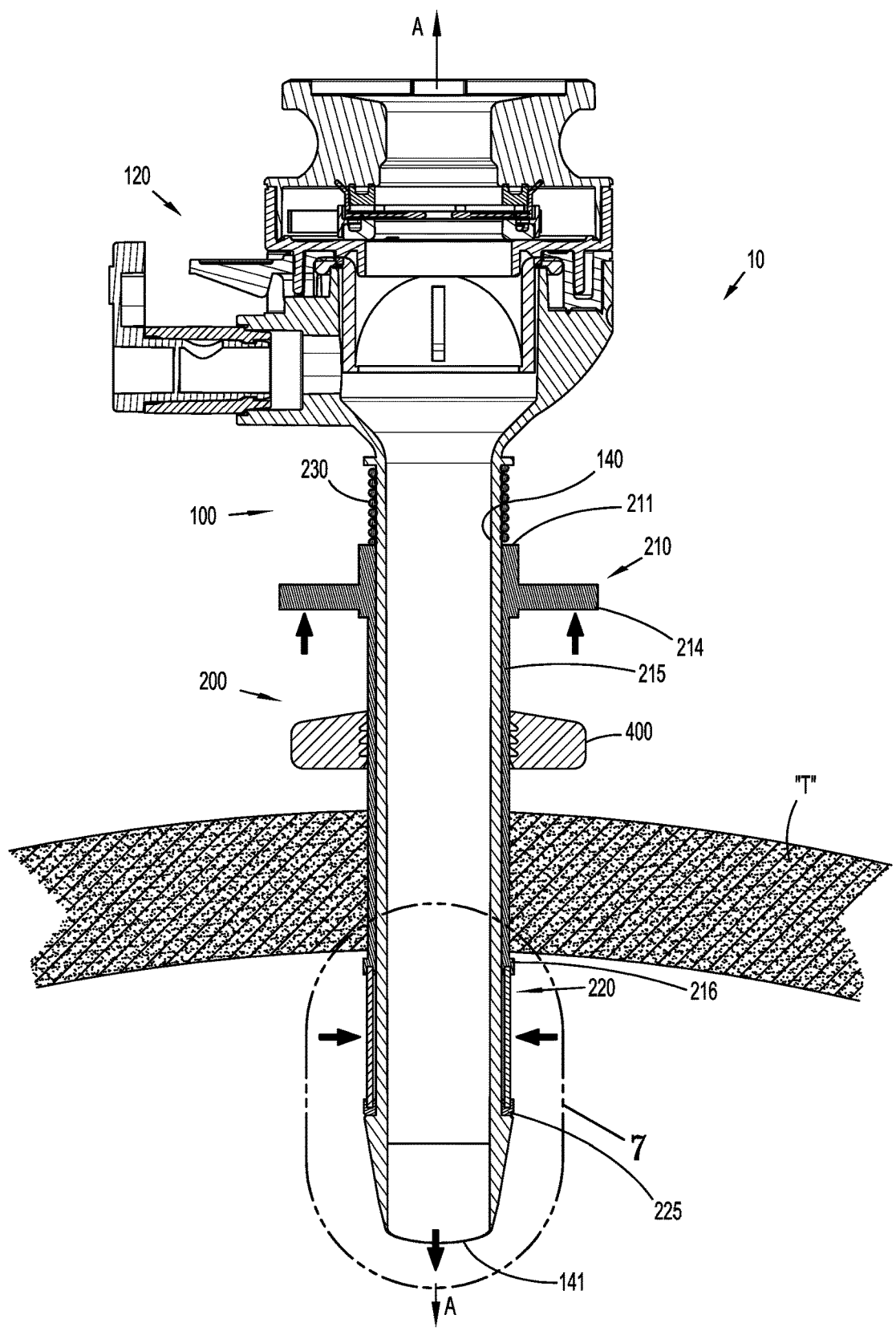
FIG. 6 is a longitudinal cross-sectional view of the surgical access device taken along section line 6-6 in FIG. 5.

With reference to FIG. 5, the expandable member 220 defines a plurality of diamond-like openings 221 around its perimeter. The openings 221 are configured such that narrow portions 221a thereof are located at the proximal end 224 and the distal end 226 of the expandable member 220, and a wide portion 221b of each opening 221 is located at or near the mid-portion 222 of the expandable member 220. This configuration allows or facilitates the expandable member 220 to effectively bend or fold (and unfold) at or near its mid-portion 222 as the fixation mechanism 200 transitions between its first position and its second position. In aspects, the expandable member 220 includes a perforation or crease at or near the mid-portion 222 to further facilitate bending and/or folding.

In various aspects, the expandable member 220 is made of rubber or plastic. Such a rubber or plastic expandable member 220 is able to retain its shape (in both the first position and the second position) without the need for the expandable member 220 to be filled with fluid (e.g., liquid or gas), for instance.

Referring now to FIGS. 1, 2, 5, 6, and 9, an anchor 400 is shown. The anchor 400 is positionable around the elongated portion 140 of the cannula body 100 such that the anchor 400 radially surrounds a portion of the elongated portion 140. The anchor 400 can either have a frictional engagement with the elongated portion 140 such that the anchor 400 can be pushed/pulled to move between longitudinal positions, or the anchor 400 can be rotationally engaged with the elongated portion 140 (e.g., a threaded connection) such that the anchor 400 can be rotated about the longitudinal axis "A-A" relative to the elongated portion 140 to move between longitudinal positions. The anchor 400 may also be fixed from longitudinal and/or rotational movement relative to the elongated portion 140.

In use, when the fixation mechanism 200 is in its first position (FIGS. 5-7) corresponding to the expandable member 220 being in its first position, and the biasing element 230 being in the compressed orientation (e.g., a user is pulling the arms 214 of the collar 210 proximally), the distal tip 141 of the elongated portion 140 of the cannula body 100 is inserted through an incision in tissue. Engagement between the anchor 400 and a proximal wall of the tissue prevents additional insertion of the cannula body 100.

To transition the fixation mechanism 200 to its second position (FIGS. 1, 3, 8, and 9), the user releases the proximal force exerted on the arms 214 thereby allowing the biasing element 230 to expand distally into its second orientation, which moves the collar 210 distally. This distal movement of the collar 210 relative to the elongated portion 140 causes the sleeve 215 and proximal ring 216 to move distally relative to the elongated portion 140 and relative to the distal ring 225. Further, as discussed above, this distal movement causes the mid-portion 222 of the expandable member 220 to move away from the elongated portion 140. In this position, the surgical access device 10 can be moved proximally relatively to the tissue "T" such that the expandable member 220 engages a distal portion of the tissue wall "T" (FIG. 9).

Next, in aspects where the anchor 400 is longitudinally movable relative the elongated portion 140 of the cannula body 100, the anchor 400 is moved distally such that the anchor 400 contacts a proximal portion of the tissue wall "T," thereby sandwiching the tissue wall "T" between the anchor 400 and the expandable member 220, and fixing the longitudinal position of the cannula body 100 relative to the tissue wall "T."

Figure 10:
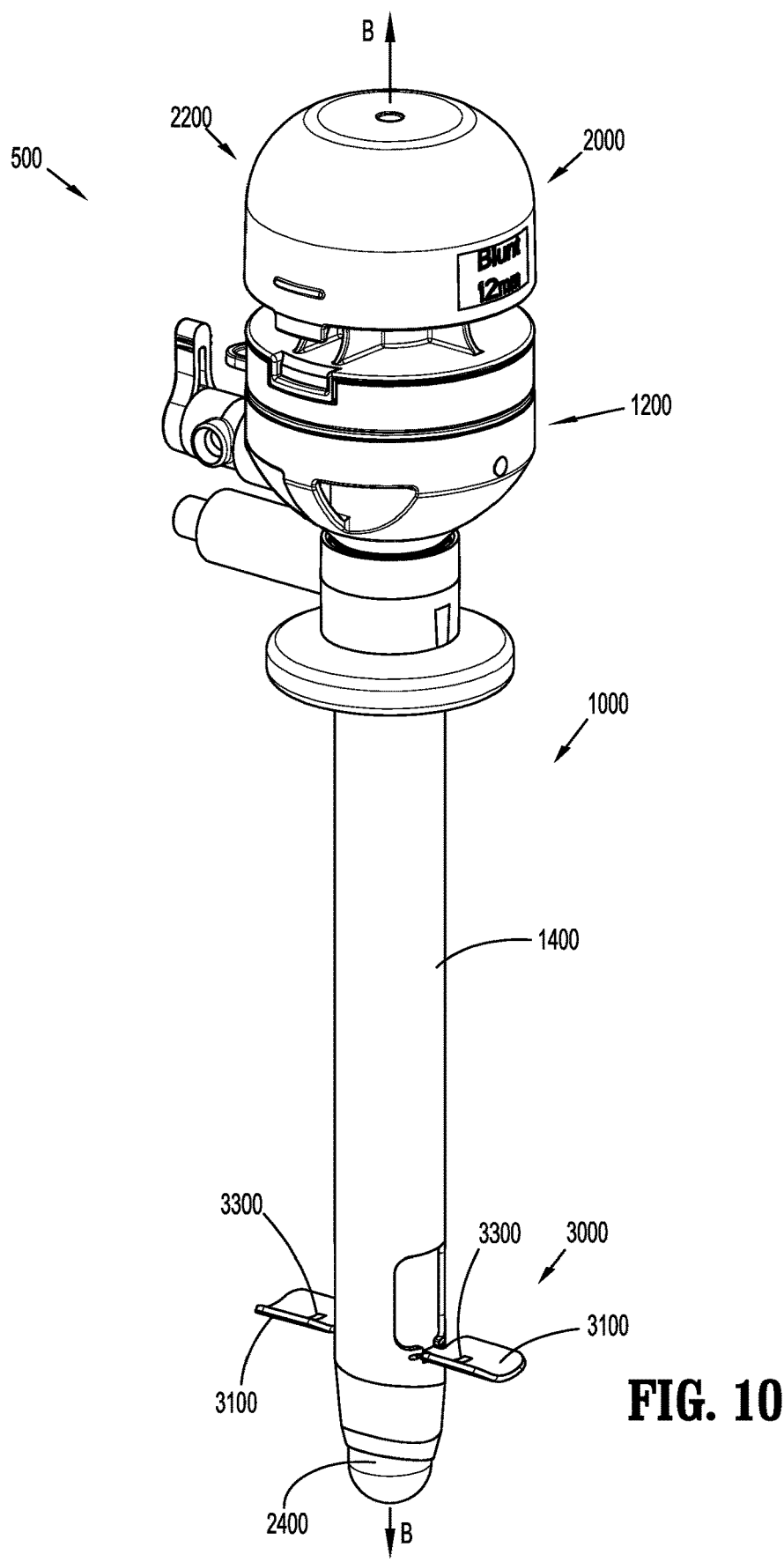
FIG. 10 is a perspective view of a surgical access device illustrating a fixation mechanism in a deployed configuration in accordance with a second aspect of the present disclosure.
Figure 11:
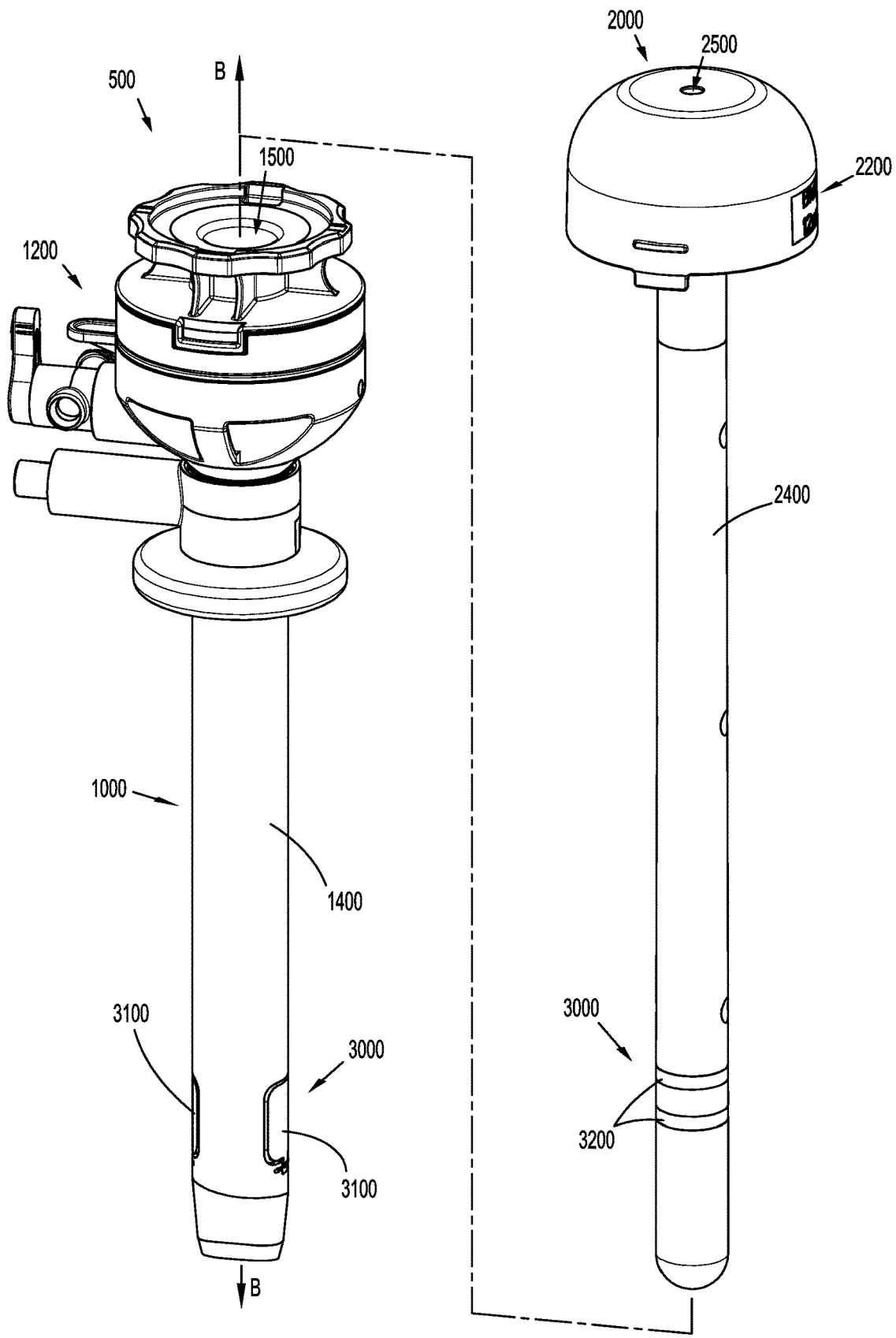
FIG. 11 is an assembly view of the surgical access device of FIG. 10.

Referring now to FIGS. 10-27, a surgical access device according to a second aspect of the present disclosure is shown. With initial reference to FIGS. 10 and 11, the surgical access device 500 includes a cannula body 1000, an obturator assembly 2000, and a fixation mechanism 3000.

The cannula body 1000 includes a housing 1200 at its proximal end and includes an elongated portion 1400 extending distally from the housing 1200. The elongated portion 1400 defines a channel 1500 (FIG. 11) extending therethrough, and defines a longitudinal axis "B-B."

The obturator assembly 2000 includes a proximal end 2200 and an elongated portion 2400 extending distally from the proximal end 2200. The elongated portion 2400 defines a channel 2500 (FIG. 11) extending therein, which is configured to allow a portion of a surgical instrument to be inserted therein. At least part of the elongated portion 2400 of the obturator assembly 2000 is insertable through the channel 1500 defined by the elongated portion 1400 of the cannula body 1000, and the proximal end 2200 of the obturator assembly 2000 is engageable with the housing 1200 of the cannula body.

The fixation mechanism 3000 includes at least one wing 3100 coupled to the elongated portion 1400 of the cannula body 1000, a first plurality of magnets 3200 disposed in mechanical cooperation with the elongated portion 2400 of the obturator assembly 2000, and a second plurality of magnets 3300 (FIGS. 19, 20, 22, 24, 25, and 27) disposed in mechanical cooperation with the at least one wing 3100 of the fixation mechanism.

As will be described in further detail below, insertion of the elongated portion 2400 of the obturator assembly 2000 through the channel 1500 of the cannula body 1000 causes the first plurality of magnets 3200 to magnetically engage the second plurality of magnets 3300, which causes the at least one wing 3100 of the fixation mechanism 3000 to move between a first position (FIGS. 11, 13, and 21-23), where the at least one wing 3100 is disposed generally parallel to the longitudinal axis "B-B", and a second position (FIGS. 10, 12, 17, 18, and 24-27), where the at least one wing 3100 is disposed generally perpendicular to the longitudinal axis "B-B."

Referring to FIGS. 12, 14, 17, and 23, the fixation mechanism 3000 includes a first wing 3100a and a second wing 3100b. Each wing 3100a, 3100b is pivotally connected to the elongated portion 1400 of the cannula body 1000, and is pivotable between a first position (FIGS. 12 and 17) where the wings 3100a, 3100b are generally perpendicular to the longitudinal axis "B-B," and a second position (FIGS. 13, 14, and 21-23) the wings 3100a, 3100b are within respective recesses 1410a, 1410b of the elongated portion 1400 and generally parallel to the longitudinal axis "B-B." Gravity biases the wings 3100a, 3100b towards the first position, and magnetic forces urge the wings 3100a, 3100b towards the second position, as described below. In aspects, the wings 3100a, 3100b may be biased towards the first position utilizing springs, for instance.

More particularly, with reference to FIGS. 12-14, each wing 3100a, 3100b includes a respective pin 3102a, 3102b extending laterally from a distal portion thereof. Each pin 3102a, 3102b mechanically engages (e.g., snap-locks) a slot 1412 of respective recesses 1410a, 1410b, thereby providing the pivotal movement between the at least one wing 3100 and the elongated portion 1400.

Additionally, while two wings 3100a, 3100b are shown, the fixation mechanism 3000 may include more or fewer wings without departing from the scope of the present disclosure.

Figure 15:
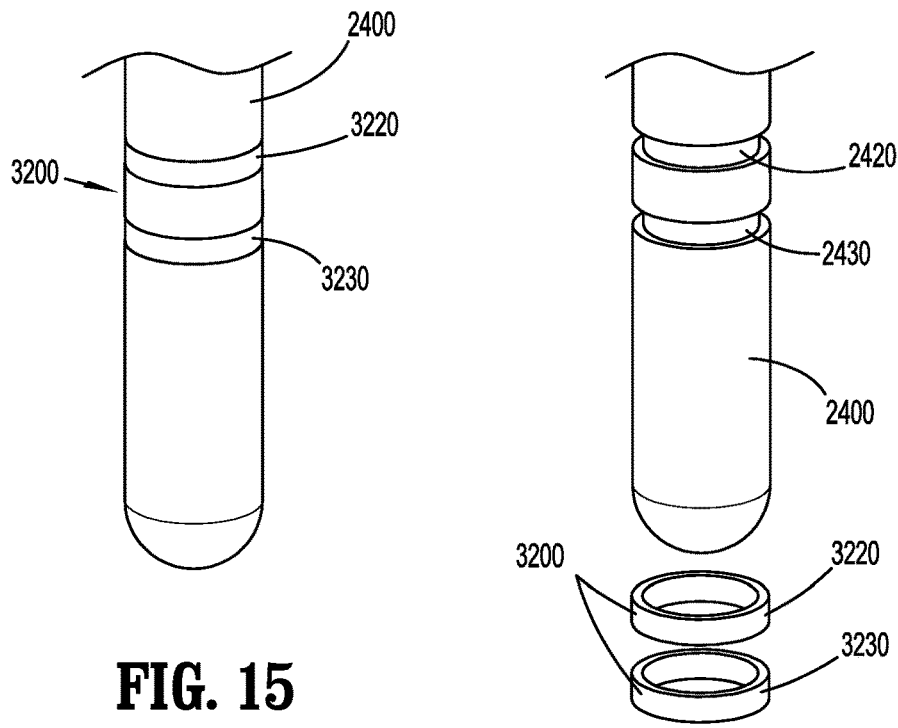
FIG. 15 is a perspective view of a distal portion of an obturator assembly including a portion of the fixation mechanism of the surgical access device of FIG. 10.
Figure 16:
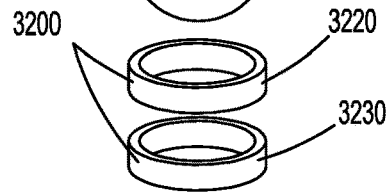
FIG. 16 is an assembly view of the distal portion of an obturator assembly and a portion of the fixation mechanism of the surgical access device of FIG. 10.

With particular reference to FIGS. 15 and 16, the first plurality of magnets 3200 includes a first magnet 3220 disposed at least partially within a first annular groove or channel 2420 within an outer wall of the elongated portion 2400 of the obturator assembly 2000, and a second magnet 3230 disposed at least partially within a second annular groove or channel 2430 with the outer wall of the elongated portion 2400 of the obturator assembly 2000. The first magnet 3220 is disposed proximally of the second magnet 3230 and has a first polarity (e.g., positive), and the second magnet 3230 has a second, opposite polarity (e.g., negative).

Figure 17:
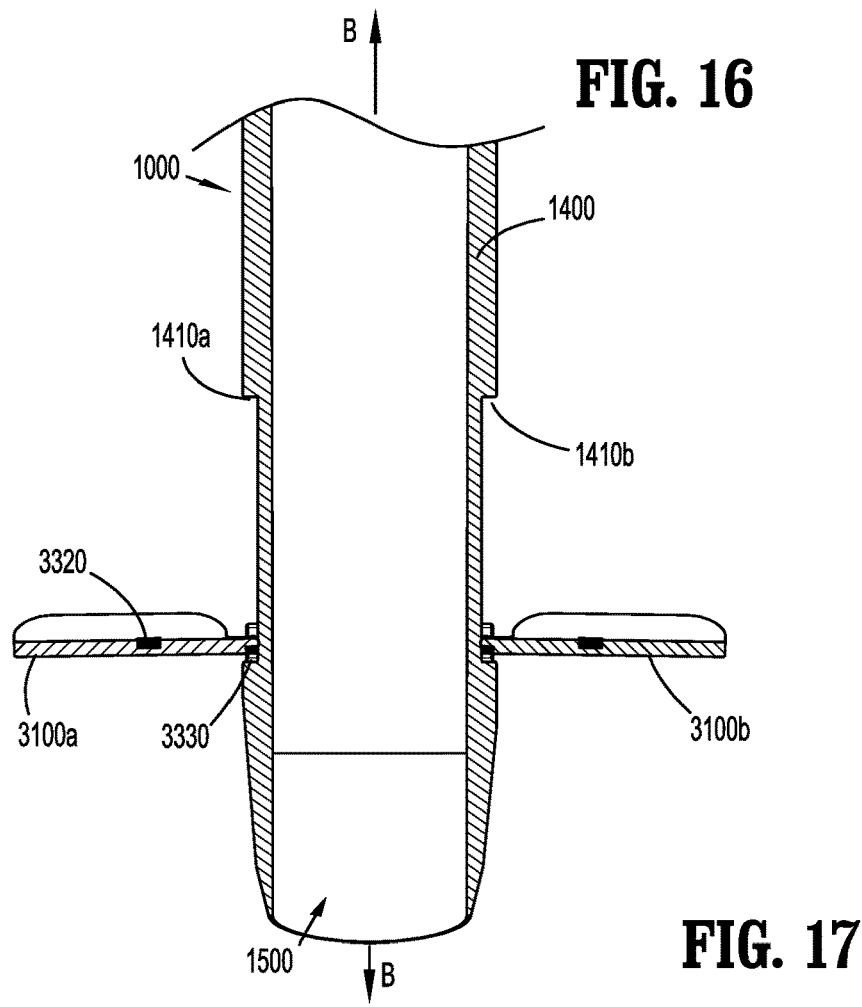
FIG. 17 is a longitudinal cross-sectional view of the surgical access device taken along section line 17-17 in FIG. 12.

With reference to FIG. 17, the second plurality of magnets 3300 includes a first magnet 3320 disposed at least partially within an inner wall of the at least one wing 3100, and a second magnet 3330 disposed at least partially within an outer all of the at least one wing 3100. The first magnet 3320 is disposed proximally of the second magnet 3330 (when the at least one wing 3100 is generally parallel to the longitudinal axis "B-B") and has the same polarity (negative) as the second magnet 3230 of the first plurality of magnets 3200. The second magnet 3330 has the same polarity (negative) as the first magnet 3320 of the second plurality of magnets 3300 and the same polarity as the second magnet 3230 of the first plurality of magnets 3200.

In the illustrated aspect, the first magnet 3220 and the second magnet 3230 of the first plurality of magnets 3200 are annular rings, such that regardless of the rotational position of the obturator assembly 2000 relative to the cannula body 1000, the first plurality of magnets 3200 will be able to magnetically engage (i.e., attract and/or repel) the second plurality of magnets 3300.

Figure 18:
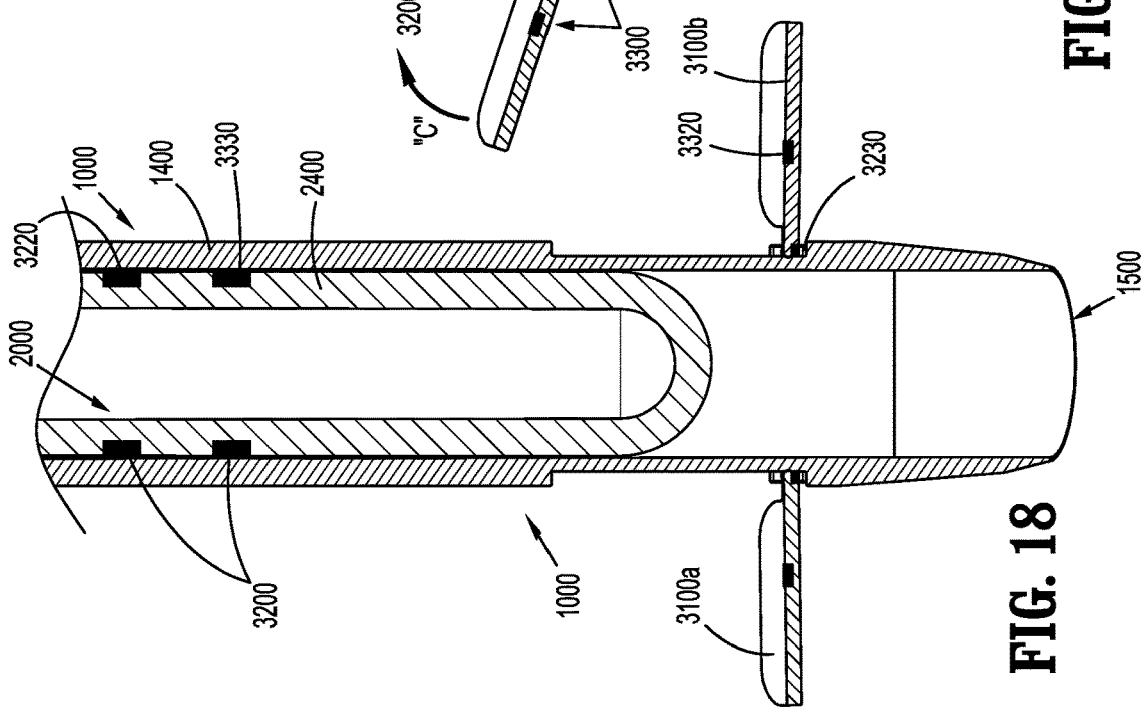

Referring now to FIGS. 17-27, various steps illustrating the use of the surgical access device 500 and the fixation mechanism 3000 are shown. FIG. 17 shows the wings 3100a, 3100b of the fixation mechanism 3000 in the first position, and prior to the elongated portion 2400 of the obturator assembly 2000 being inserted through the channel 1500 of the cannula body 1000. In FIG. 18, part of the elongated portion 2400 of the obturator assembly 2000 is within the channel 1500 of the cannula body 1000. The first plurality of magnets 3200 of the elongated portion 2400 of the obturator assembly 2000 are too far from the second plurality of magnets 3300 of the at least one wing 3100 to result in any perceptible magnetic forces therebetween.

Figure 20:
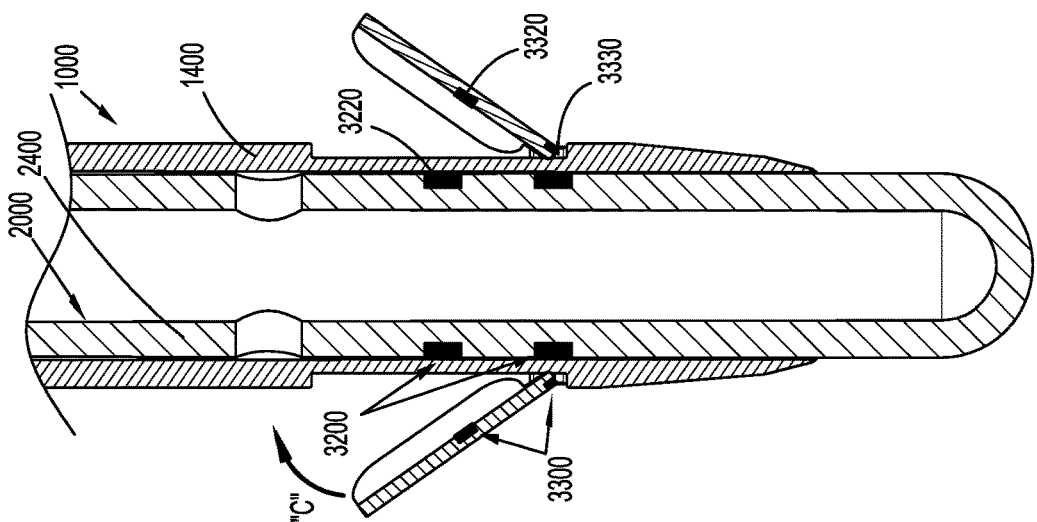
FIGS. 18-20 are longitudinal cross-sectional views of a distal portion of the surgical access device of FIG. 10 illustrating portions of the fixation mechanism at various stages of retraction.
Figure 19:
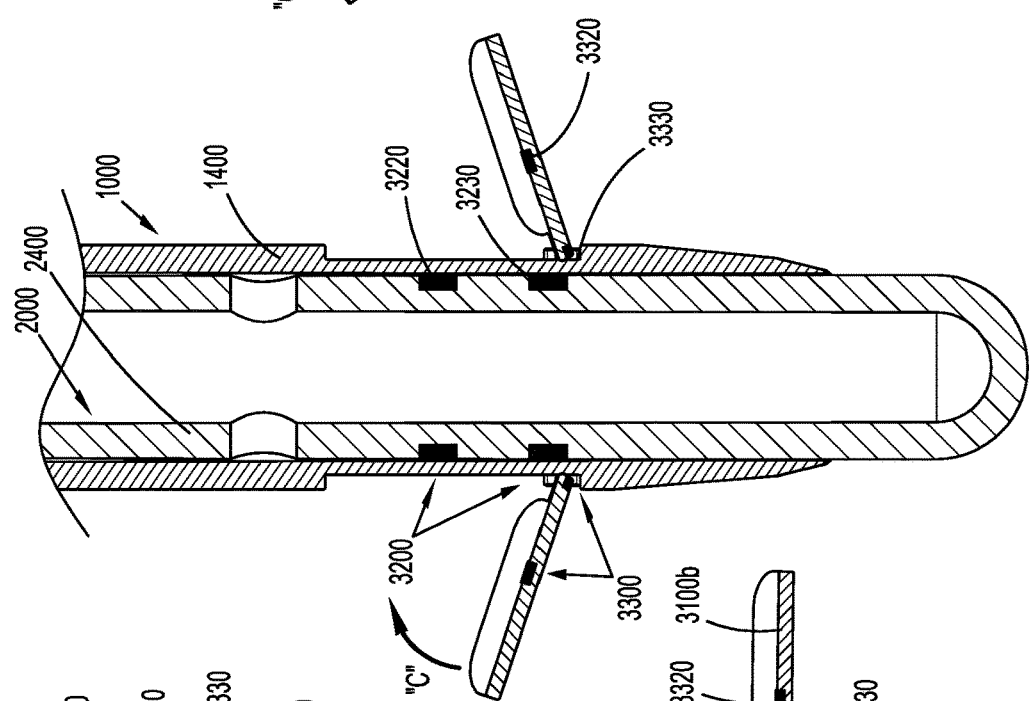

Referring to FIGS. 19 and 20, the pivoting of the wings 3100a, 3100b as the first plurality of magnets 3200 of the elongated portion 2400 magnetically engages the second plurality of magnets 3300 of the wings 3100a, 3100b is shown. In particular, when the distal or second magnet 3230 of the first plurality of magnets 3200 is advanced longitudinally such that the second magnet 3230 is approximately aligned with the distal or second magnet 3330 of the second plurality of magnets 3300, the second magnet 3230 of the first plurality of magnets 3200 repels the second magnet 3330 of the second plurality of magnets 3300, resulting in the wings 3100a, 3100b pivoting in the general direction of arrow "C" towards their second position, where insertion of the distal portion of the cannula body 1000 into tissue is facilitated.

Figure 22:
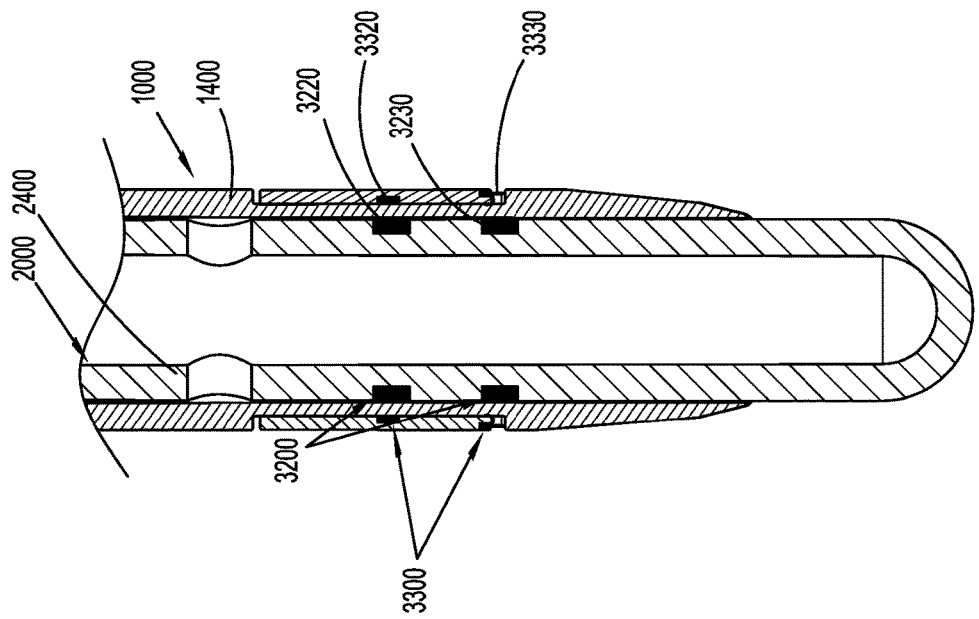
FIG. 22 is a longitudinal cross-sectional view of the surgical access device taken along section line 22-22 in FIG. 21.
Figure 21:
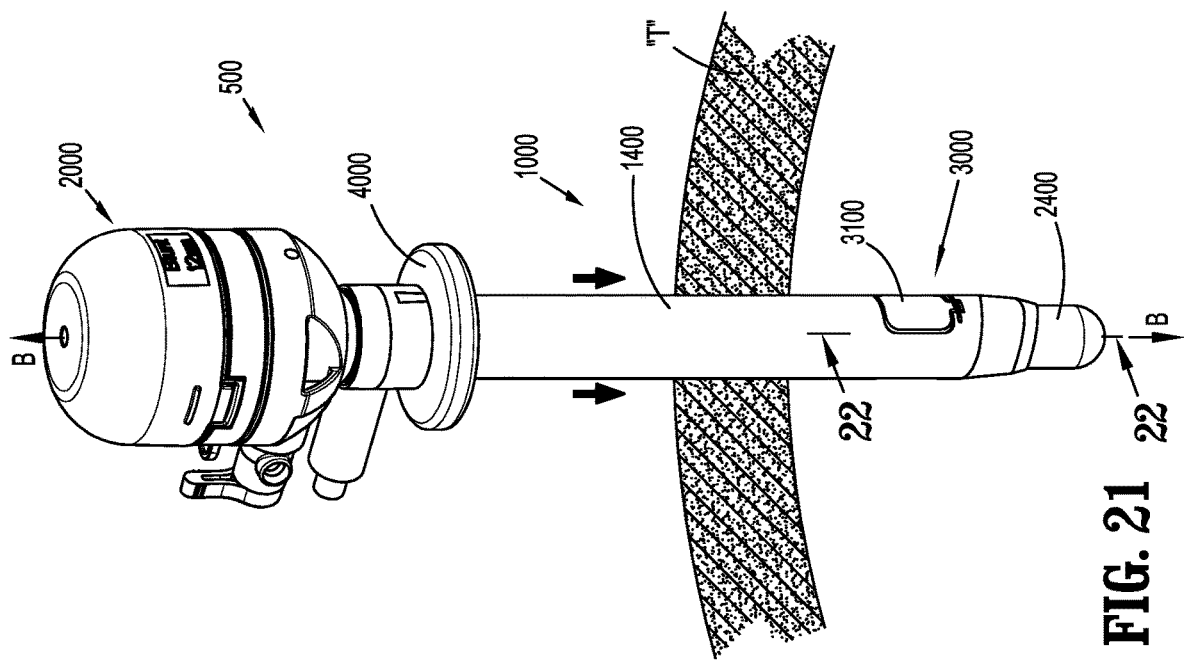
FIG. 21 is a perspective view of the surgical access device of FIG. 10 illustrating a portion of the fixation mechanism within tissue and in an undeployed configuration.

FIGS. 21 and 22 show the elongated portion 2400 of the obturator assembly 2000 fully advanced within the channel 1500 of the cannula body 1000, and the wings 3100a, 3100b in their second position. In addition to the second magnet 3230 of the first plurality of magnets 3200 repelling the second magnet 3330 of the second plurality of magnets 3300, the first magnet 3220 of the first plurality of magnets 3200 attracts the oppositely-polarized first magnet 3320 of the second plurality of magnets 3300. In this position, the distal portion of the surgical access device 500 can be inserted into tissue "T" (FIG. 21).

Figure 23:
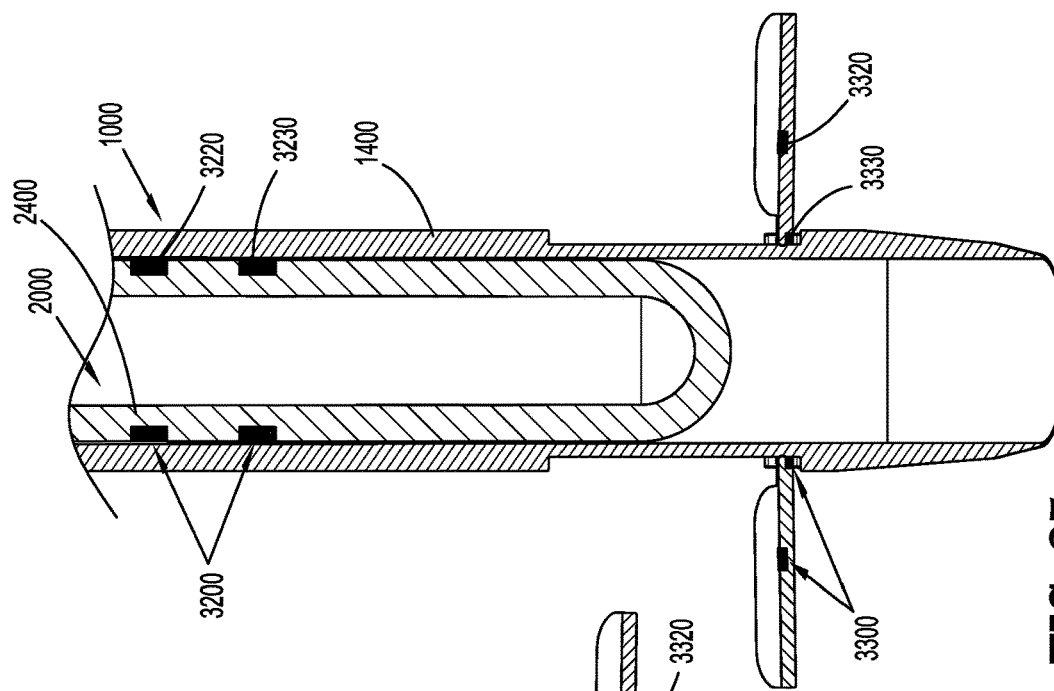
FIGS. 23-25 are longitudinal cross-sectional views of a distal portion of the surgical access device of FIG. 10 illustrating portions of the fixation mechanism at various stages of deployment.
Figure 24:
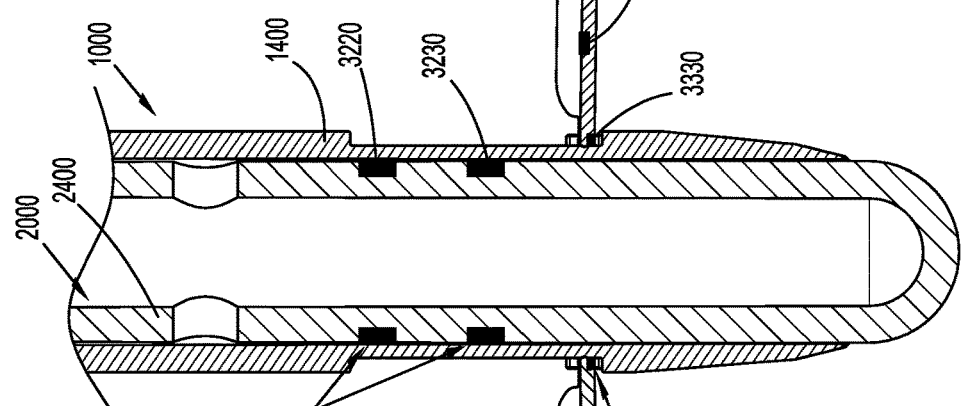
Figure 25:
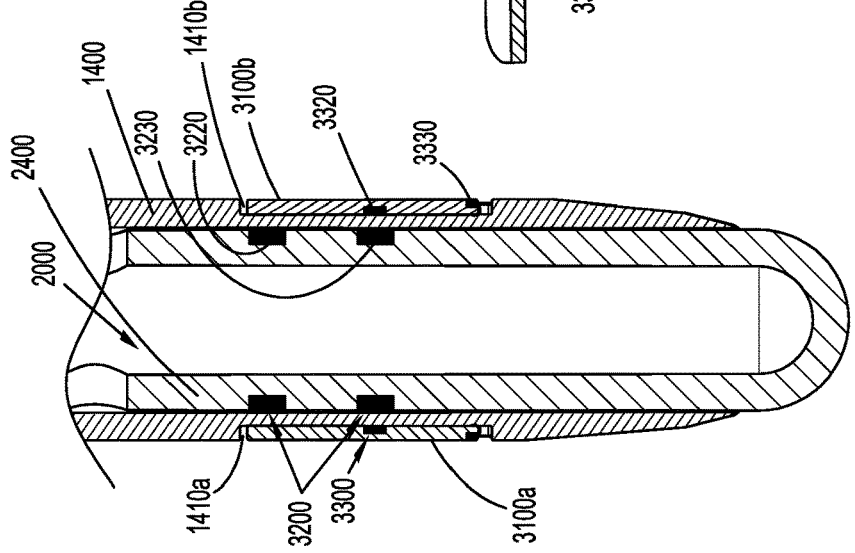

Referring now to FIGS. 23-25, to return the wings 3100a, 3100b to their first position (e.g., when the wings 3100a, 3100b are within tissue "T"), the obturator assembly 2000 is moved proximally relative to the cannula body 1000. During proximal movement of the obturator assembly 2000, the first plurality of magnets 3200 on the elongated portion 2400 on the obturator assembly 2000 moves proximally relative to the second plurality of magnets 3300 on the wings 3100a, 3100b. In the position shown in FIGS. 23 and 24, the second magnet 3230 of the first plurality of magnets 3200 is in longitudinal alignment with the first magnet 3320 of the second plurality of magnets 3300. Since these magnets have opposite polarities, the wings 3100a, 3100b, which include the first magnet 3320 of the second plurality of magnets 3300, are repelled (and acted on by gravity) such that the wings 3100a, 3100b are pivoted in the general direction of arrow "D" towards their first position. FIG. 25 shows the elongated portion 2400 of the obturator assembly 2000 move farther proximally, while the wings 3100a, 3100b remain in their first position.

Figure 27:
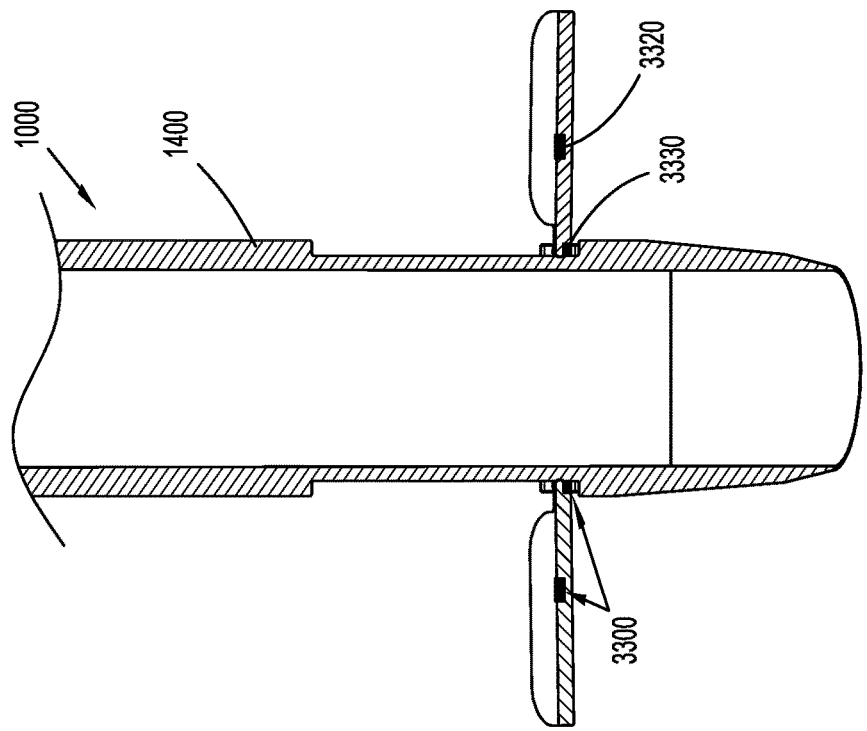
FIG. 27 is a longitudinal cross-sectional view of the area of detail indicated in FIG. 26.
Figure 26:
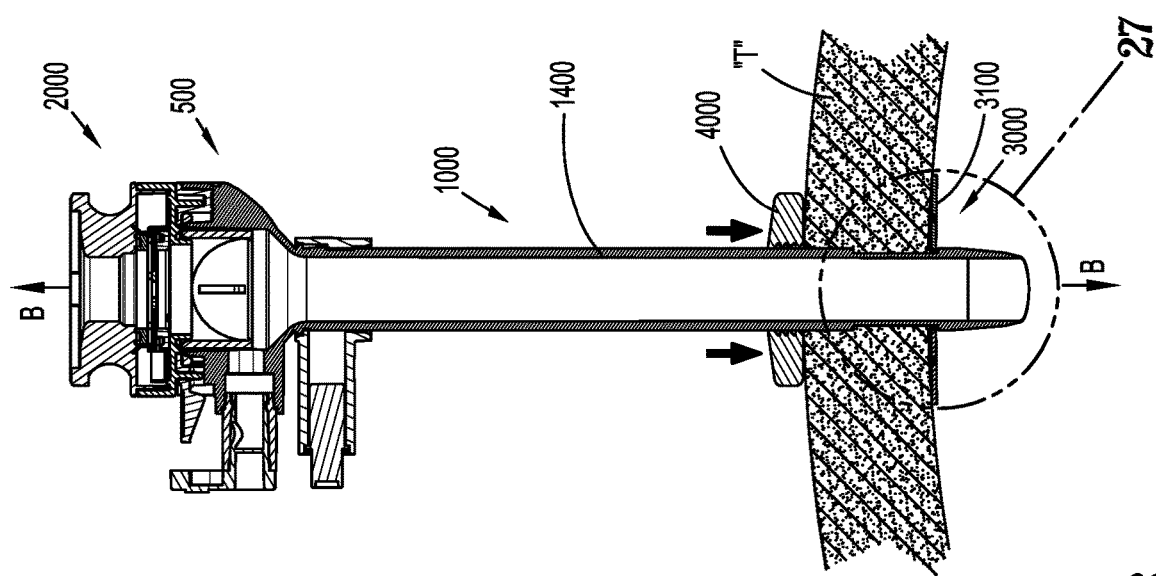
FIG. 26 is a longitudinal cross-sectional view of the surgical access device of FIG. 10 illustrating a portion of the fixation mechanism within tissue and in a deployed configuration.

With reference to FIGS. 26 and 27, the wings 3100a, 3100b are in their first position and the obturator assembly 2000 has been removed from the cannula body 1000. Here, the cannula body 1000 can be moved proximally relative to the tissue "T" such that wings 3100a, 3100b contact a distal wall of the tissue "T" and resist further proximal movement of the cannula body 1000 relative to the tissue "T." Next, in aspects where an anchor 4000 is used, the anchor 4000 is moved distally such that the anchor 4000 contacts a proximal portion of the tissue "T," thereby sandwiching the tissue "T" between the anchor 4000 and the wings 3100a, 3100b, and fixing the longitudinal position of the cannula body 1000 relative to the tissue "T."

While the above description contains many specifics, these specifics should not be construed as limitations on the scope of the present disclosure, but merely as illustrations of various aspects thereof. Therefore, the above description should not be construed as limiting, but merely as exemplifications of various aspects. Those skilled in the art will envision other modifications within the scope and spirit of the claims appended hereto.

What is claimed is:

1. A surgical access device, comprising:
   a cannula body including a housing and an elongated portion extending distally from the housing, the elongated portion defining a longitudinal axis, and defining a channel;
   an obturator assembly including a housing and an elongated portion extending distally from the housing of the obturator assembly, at least part of the elongated portion of the obturator assembly configured to be inserted through the channel of the elongated portion of the cannula body; and
   a fixation mechanism including:
      at least one wing coupled to the elongated portion of the cannula body, the at least one wing movable relative to the elongated portion of the cannula body between a first position where the at least one wing is parallel to the longitudinal axis, and a second position where the at least one wing is disposed at an angle to the longitudinal axis;
      a first plurality of magnets disposed on the elongated portion of the obturator assembly, the first plurality of magnets including a first magnet having a first polarity; and
      a second plurality of magnets disposed on the at least one wing, the second plurality of magnets including a first magnet having the first polarity;
      wherein a predetermined amount of translation of the elongated portion of the obturator assembly within the channel of the elongated portion of the cannula body is configured to cause the at least one wing to move from the first position to the second position.

2. The surgical access device according to claim 1, wherein the predetermined amount of translation is a predetermined amount of proximal translation of the obturator assembly relative to the cannula body and is configured to cause the at least one wing to move from the first position to the second position.

3. The surgical access device according to claim 2, wherein a predetermined amount of distal translation of the obturator assembly relative to the cannula body is configured to cause the at least one wing to move from the second position to the first position.

4. The surgical access device according to claim 1, wherein the at least one wing includes a first wing and a second wing.

5. The surgical access device according to claim 1, wherein a second magnet of the first plurality of magnets has a second polarity, the first polarity being opposite from the second polarity.

6. The surgical access device according to claim 1, wherein the first magnet of the first plurality of magnets defines an annular ring.

7. The surgical access device according to claim 6, wherein the first plurality of magnets includes a second magnet defining an annular ring.

8. The surgical access device according to claim 1, wherein the at least one wing is biased towards the second position.

9. The surgical access device according to claim 1, wherein a second magnet of the second plurality of magnets has the first polarity.

10. The surgical access device according to claim 9, wherein the first magnet of the second plurality of magnets is on an inner surface of the at least one wing and the second magnet of the second plurality of magnets is on an outer surface of the at least one wing.

11. A surgical access device, comprising:
    a cannula body including a housing and an elongated portion extending distally from the housing, the elongated portion defining a longitudinal axis, and defining a channel; and
    a fixation mechanism including:
       a wing pivotably engaged with the elongated portion of the cannula body and movable between a first position where the wing is parallel to the longitudinal axis, and a second position where the wing is disposed at an angle to the longitudinal axis;
       a first magnet having a first polarity and being disposed on the wing; and
       a second magnet having a second polarity and being disposed on the wing, the first polarity being opposite from the second polarity, wherein a predetermined amount of translation of an obturator assembly within the channel of the elongated portion of the cannula body causes is configured to cause the wing to move from the first position to the second position.

12. The surgical access device according to claim 11, wherein the first magnet is disposed proximally of the second magnet when the wing is in the first position.

13. The surgical access device according to claim 11, wherein when the wing is in the second position, the wing is perpendicular to the longitudinal axis.

14. The surgical access device according to claim 13, wherein the wing is biased towards the second position.

15. A surgical access device, comprising:
 a cannula body defining a longitudinal axis and defining a channel; and
 a fixation mechanism including:
  a wing coupled to the cannula body and movable between a first position where the wing is parallel to the longitudinal axis, and a second position where the wing is disposed at an angle to the longitudinal axis;
  a first magnet disposed on the wing; and
  a second magnet disposed on the wing, the first magnet having a first polarity and the second magnet having a second polarity, the first polarity being opposite from the second polarity,
 wherein a predetermined amount of translation of a translatable magnet within the channel of the cannula body is configured to cause the wing to move from the first position to the second position.

16. The surgical access device according to claim 15, wherein the first magnet is disposed on an inner surface of the wing, and the second magnet is disposed on an outer surface of the wing.

17. The surgical access device according to claim 15, wherein the first magnet is disposed on an inner surface of the wing.

18. The surgical access device according to claim 15, wherein the wing is biased towards the second position.

* * * * *